United States Patent

White et al.

[11] 3,971,782
[45] July 27, 1976

[54] FLUORENE DERIVATIVES

[75] Inventors: Alan Chapman White, Windsor; Robin Michael Black, Porton, both of England

[73] Assignee: John Wyeth & Brother, Maidenhead, England

[22] Filed: Nov. 4, 1975

[21] Appl. No.: 628,621

[30] Foreign Application Priority Data
Nov. 20, 1974 United Kingdom............... 50180/74

[52] U.S. Cl............................. 260/251 R; 260/309.6
[51] Int. Cl.².............. C07D 233/06; C07D 239/06
[58] Field of Search..................... 260/251 R, 309.6

[56] References Cited
UNITED STATES PATENTS

| | | | |
|---|---|---|---|
| 2,948,424 | 8/1960 | Sahyun et al. | 260/251 |
| 3,833,655 | 9/1974 | Edenhofer et al. | 260/251 X |
| 3,888,846 | 6/1975 | Metlesics et al. | 260/251 X |

*Primary Examiner*—Lewis Gotts
*Assistant Examiner*—Dolph H. Torrence
*Attorney, Agent, or Firm*—Richard K. Jackson

[57] ABSTRACT

The invention relates to fluorene derivatives of the formula

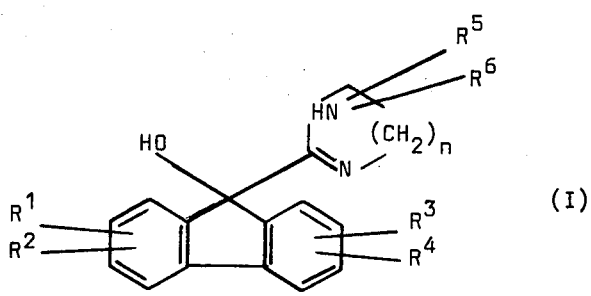

and their pharmaceutically acceptable acid addition salts. In the formula $R^1$, $R^2$, $R^3$ and $R^4$ each represent hydrogen, hydroxyl, lower alkyl, lower alkoxy or halogen, $R^5$ and $R^6$ each represent hydrogen or lower alkyl and $n$ represents 1 or 2. The compounds have hypoglycaemic activity.

3 Claims, No Drawings

FLUORENE DERIVATIVES

This invention relates to fluorene derivatives. In particular, the invention relates to certain novel fluorene derivatives, to methods of preparing the novel derivatives and to pharmaceutical compositions containing them.

The novel fluorene derivatives of the present invention are compounds of general formula (I)

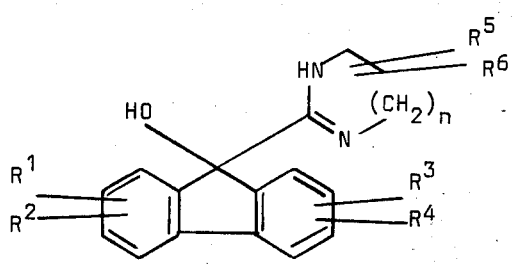

(I)

and their pharmaceutically acceptable acid addition salts.

In general formula (I) $R^1$, $R^2$, $R^3$ and $R^4$ each represent hydrogen, hydroxyl, lower alkyl, lower alkoxy or halogen, $R^5$ and $R^6$ each represents hydrogen or lower alkyl and n represents 1 or 2.

The term "lower" as used herein means that the radical referred to contains 1 to 6 carbon atoms. Preferably the radical contains 1 to 4 carbon atoms.

In formula (I) n preferably represents 2. Thus the preferred compounds are 9-(1,4,5,6-tetrahydro-2-pyrimidinyl) 9H-fluoren-9-ol derivatives of general formula (II)

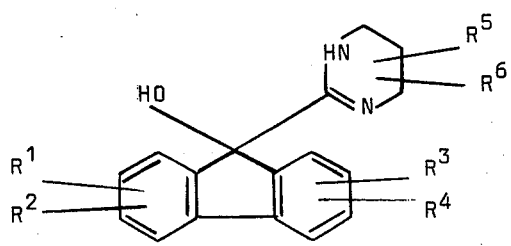

(II)

and their pharmaceutically acceptable acid addition salts.

The substituents $R^1$, $R^2$, $R^3$ and $R^4$ can be the same or different and each represent hydrogen, lower alkyl (e.g. methyl, ethyl, propyl or butyl), lower alkoxy (e.g. methoxy, ethoxy, propoxy or butoxy) or halogen (e.g. chlorine or bromine). Preferred compounds are those in which $R^1$, $R^2$, $R^3$ and $R^4$ are all hydrogen.

The substituents $R^5$ and $R^6$ can be the same or different i.e. one can be hydrogen and the other lower alkyl (e.g. methyl, ethyl, propyl or butyl), both can be hydrogen or both can be lower alkyl. When $R^5$ and $R^6$ are both lower alkyl they can be attached to the same carbon atom or different carbon atoms. Preferably $R^5$ and $R^6$ are both hydrogen.

A particularly preferred class of compounds are those of the general formula

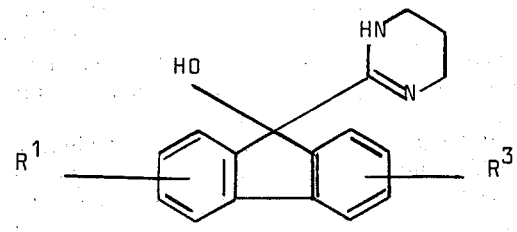

and their pharmaceutically acceptable acid addition salts, wherein $R^1$ is hydrogen, hydroxyl, lower alkyl, lower alkoxy or halogen and $R^3$ is hydrogen or halogen.

The compounds of the invention can be prepared by reacting a diamine of general formula (III)

$$NH_2\text{-}A\text{-}NH_2 \qquad (III)$$

(wherein A is a polymethylene chain of 2 or 3 carbon atoms substituted on the same or different carbon atoms by the groups $R^5$ and $R^6$, where $R^5$ and $R^6$ have the meanings given above) with an imidate of general formula (IV)

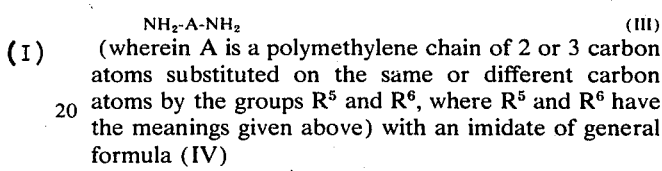

(IV)

or an acid addition salt thereof (in which $R^1$, $R^2$, $R^3$ and $R^4$ have the meanings given above in connection with formula I and R is a lower alkyl group) or with an amidine of general formula

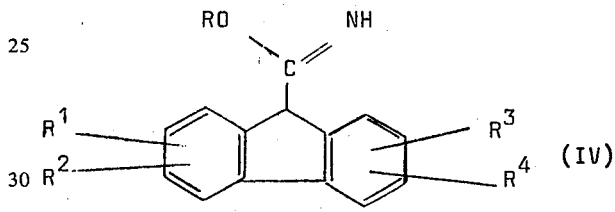

(V)

or an acid addition salt thereof (wherein $R^1$, $R^2$, $R^3$ and $R^4$ have the meanings given above in connection with formula I) and, if required, oxidising any product of general formula (VI)

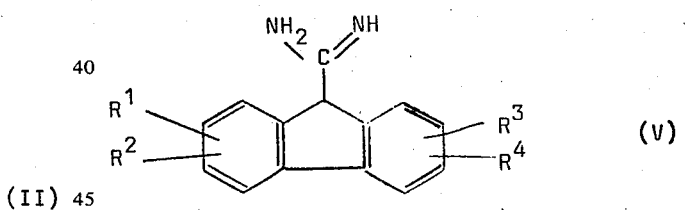

(VI)

The reaction of the diamine with the imidate or amidine is preferably carried out in an organic solvent. Generally the product of the reaction is the desired compound of general formula (I), any product of formula (VI) being spontaneously oxidised either during the reaction or during the isolation of the product from the reaction medium. However, if a product of general formula (VI) is isolated it may be oxidised e.g. by passing oxygen or air through a solution of the compound in a solvent (e.g. benzene, t-butanol or dimethylsulphoxide).

Preferably the diamine is reacted with the imidate of general formula (IV), particularly with an acid addition salt thereof. In general formula (IV), R is preferably ethyl.

The amidines of general formula (V) or their acid addition salts may be prepared by treating the corresponding imidates of general formula (IV) with ammonia. The imidates can be prepared by known methods, for example, by acid-catalysed addition of an alcohol of general formula ROH to a 9-cyanofluorene of general formula (VIII).

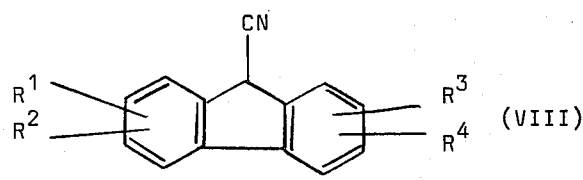

(where $R^1$, $R^2$, $R^3$, and $R^4$ have the meanings given above). In the acid-catalyzed addition of the alcohol to the nitrile the acid can be, for example, hydrogen chloride and the alcohol is preferably ethanol.

The nitriles of general formula (VII) are known compounds or they can be prepared by procedures known for preparing analogos compounds (for example a 9H-fluorene carboxaldehyde may be oximated and dehydrated or a 9H-fluorene-9-carboxylic acid or an ester thereof may be amidated and dehydrated).

If the compound of the invention is obtained as an acid addition salt, the free base can be obtained by basifying a solution of the acid addition salt. Conversely if the product is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds. Examples of suitable acids that may be used include hydrochloric, hydrobromic, tartaric, phosphoric, maleic, citric, methanesulphonic and p-toluene sulphonic acids.

The compounds of the invention may possess an asymmetric carbon atom and hence optical enantiomorphs are possible.

The compounds of the invention may be in the form of specific optical isomers or mixtures of such isomers, such as racemates. The optical isomers may be prepared from a racemic mixture by the use of standard methods described in the literature.

The compounds of the invention possess hypoglycaemic activity as indicated by standard tests on warm-blooded animals. In one such procedure male rats are fasted overnight, a control blood sample is then taken rom the tail and the test compound is then administered at a dose of 50 mg/kg by stomach tube. Subsequent blood samples are then taken at hourly intervals and the depression in blood sugar concentration relevant to the control sample is noted. In this procedure it was found that 9-(1,4,5,6-tetrahydro-2-pyrimidinyl)-9H-fluoren-9-ol, a representative compound of the present invention, produced a depression in blood sugar concentration of at least 30% in two of the hourly samples.

The invention further provides a pharmaceutical composition which comprises a compound of formula (I) or a pharmaceutically acceptable acid addition thereof, in association with a pharmaceutically acceptable carrier. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these packaged form. The quantity of active ingredient in a unit dose of composition may be carried or adjusted from 5 mg. or less to 500 or more, according to the particular need and the activity of the active ingredient. The invention also includes the compounds in the absence or carrier where the compounds are in unit dosage form.

The daily dose of compound will vary depending upon the route of administration, the particular compound employed and the particular animal involved. The daily dose could be, for example, within the range 0.5 to 25 mg/kg depending upon the method of administration and the specific compound.

The following Examples illustrate the invention:

EXAMPLE 1 a. 9H-Fluorene-9-carboximidic acid ethyl ester

Dry hydrogen chloride was passed for 3 hours into a solution of 9-cyanofluorene (15 67.85; g.; see, for example, J. Amer. Chem. Soc., 1949, 71, 1500) in ether (1 l.) ans absolute ethanol (45 ml.) at 0°C. The mixture was left at 0°C overnight, the solid filtered, washed with ether and dried under vacuum at room temperature to give the title compound as its hydrochloride hemihydrate (17.61 g., m.p. 262°–263°C dec.). Found: C, 68.5; H, 6.05; N, 4.95%. $C_{16}H_{13}NO.HCl.½H_2O$ requires C, 687.85; H, 6.05; N, 4.95%.

b. 9-(1,4,5,6-Tetrahydro-2-pyrimidinyl)-9H-fluoren-9-ol 1,3-Diaminopropane (4.92 ml.) was added dropwise to a stirred, ice-cooled suspension of 9H-fluorene-9-carboximidic acid ethyl ester hydrochloride (14.8 g.) in absolute ethanol (100 ml.). The mixture was stirred for 30 minutes at 0°C, 30 minutes at room temperature and then heated under reflux overnight (16 hours). After evaporation of the ethanol the residue was dissolved in 2N hydrochloric acid, extracted once with ether and then basified (2N NaOH). The precipitate was filtered and recrystallised from isopropanol/ether to give the crude title compound (4.012 g.). The hydrochloride salt of the title compound crystallised from isopropanol/ethereal HCl, m.p. 242°–245°. Found: C, 67.6; H, 5.95; N, 9.05%. $C_{17}H_{16}N_2O.HCl$ requires C, 67.9; H, 5.7; N, 9.3%.

EXAMPLE 2 a. 2,7-Dibromo-9H-fluorene-9-carboximidic acid ethyl ester

Dry hydrogen chloride is passed into a solution of 2,7-dibromo-9H-fluorene-9-carbonitrile [obtainable e.g. from the corresponding 2,7-dibromo-9H-fluorene carboxaldehyde (J. Org. Chem., 1944, 9, 155) by oximation and dehydration] by a process analogous to that described in Example 1(a). After working up by a procedure similar to that described in Example 1(a) the product can be used crude or purified before use in Example 2(b) below.

b. 2,7-Dibromo-9-(1,4,5,6-tetrahydro-2-pyrimidinyl)-9H-fluorene-9-ol 1,3-Diaminopropane (10 mM) is added dropwise to an ice-cold solution of 2,7-dibromo-9H-fluorene-9-carboximidic acid ethyl ester (10 mM) by a procedure analgous to that described in Example 1(b). After reaction and work up of the mixture by a process similar to that described in Example 1(b), the title produce is obtained.

EXAMPLE 3 a. By a process analogous to that described in Example 1(a) the following nitriles are converted into the corresponding imidic acid esters:

| | Nitrile | Imidic acid ester |
|---|---|---|
| (1) | 2,7-Dichloro-9H-fluorene-9-carbonitrile [obtainable from the corresponding 2,7-dichloro-9H-fluorene-9-carboxylic acid (J.Chem.Soc., 1954, 3116) by amidation and dehydration] | 2,7-Dichloro-9H-fluorene-9-carboximidic acid ethyl ester |
| (2) | 2-Ethyl-9H-fluorene-9-carbonitrile [obtainable from the corresponding 2-ethyl-9H-fluorene-9-carboxylic acid (J.Chem.Soc., 1959, 2337) by amidation and dehydration] | 2-Ethyl-9H-fluorene-9-carboximidic acid ethyl ester |
| (3) | 2-Methyl-9H-fluorene-9-carbonitrile [obtainable from the corresponding 2-methyl-9H-fluorene-9-carboxylic acid (J.Chem.Soc., 1959, 2337) by amidation and dehydration] | 2-Methyl-9H-fluorene-9-carboximidic acid ethyl ester |
| (4) | 2-Methoxy-9H-fluorene-9-carbonitrile [obtainable from 2-methyl-9H-fluorene-9-carboxylic acid (J.Chem.Soc., 1959, 237) by amidation and dehydration] | 2-Methoxy-9H-fluorene-9-carboximidic acid ethyl ester |
| (5) | 2-Chloro-9H-fluorene-9-carbonitrile [obtainable from 2-chloro-9H-fluorene-9-carboxylic acid methyl ester (Ber., 1963, 96, 2577) by amidation and dehydration] | 2-Chloro-9H-fluorene-9-carboximidic acid ethyl ester | b. The imidic acid esters of Example 3(a) are converted by procedures analogous to that described in Example 1(b) to the corresponding 9-(1,4,5,6-tetrahydro-2-pyrimidinyl)-9H-fluoren-9-ols:

| | Imidic acid ester | 9-(1,4,5,6-Tetrahydro-2-pyrimidinyl)-9H-fluoren-9-ol |
|---|---|---|
| (1) | 2,7-Dichloro-9H-fluorene-9-carboximidic acid ethyl ester | 2,7-Dichloro-9-(1,4,5,6-tetrahydro-2-pyrimidinyl)-9H-fluoren-9-ol |
| (2) | 2-Ethyl-9H-fluorene-9-carboximidic acid ethyl ester | 2-Ethyl-9-(1,4,5,6-tetrahydro-2-pyrimidinyl)-9H-fluoren-9-ol |
| (3) | 2-Methyl-9H-fluorene-9-carboximidic acid ethyl ester | 2-Methyl-9-(1,4,5,6-tetrahydro-2-pyrimidinyl)-9H-fluoren-9-ol |
| (4) | 2-Methoxy-9H-fluorene-9-carboximidic acid ethyl ester | 2-Methoxy-9-(1,4,5,6-tetrahydro-2-pyrimidinyl)-9H-fluoren-9-ol |
| (5) | 2-Chloro-9H-fluorene-9-carboximidic acid ethyl ester | 2-Chloro-9-(1,4,5,6-tetrahydro-2-pyrimidinyl)-9H-fluoren-9-ol |

EXAMPLE 4

9-(2-Imidazolinyl)-9H-fluoren-9-ol 1,2-Diaminoethane is reacted with 9H-fluorene-9-carboximidic acid ethyl ester and the product isolated by a procedure analogous to that described in Example 1(b) to give the title compound.

We claim:

1. A compound selected from the group consisting of a fluorene derivative of formula

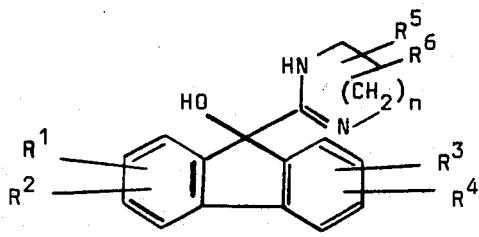
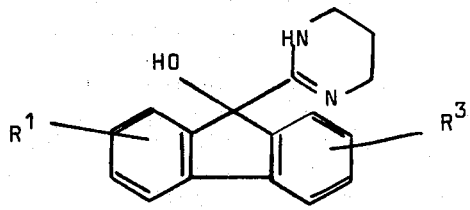

and a pharmaceutically acceptable acid addition salt thereof, wherein $R^1$, $R^2$, $R^3$ and $R^4$ each represents a member from the group consisting of hydrogen, hydroxyl, lower alkyl, lower alkoxy and halogen, $R^5$ and $R^6$ each represents a member from the group consisting of hydrogen and lower alkyl and n represents 1 or 2.

2. A compound as claimed in claim 1 of which is a fluorene derivative of formula or a pharmaceutically acceptable acid addition salt thereof wherein $R^1$ is selected from the group consisting of hydrogen, hydroxyl, lower alkyl, lower alkoxy and halogen and $R^3$ is selected from the group consisting of hydrogen and halogen.

3. A compound as claimed in claim 1 which 9-(1,4,5,6-tetrahydro-2-pyrimidinyl)-9H-fluoren-9-ol.

* * * * *